United States Patent
Saiki et al.

(10) Patent No.: US 10,011,704 B2
(45) Date of Patent: Jul. 3, 2018

(54) RUBBER COMPOSITION, TIRE, BISPHENYLDIAMINE COMPOUND, AND ANTI-AGING AGENT

(71) Applicant: OTSUKA CHEMICAL CO., LTD., Osaka-shi, Osaka (JP)

(72) Inventors: Aya Saiki, Kunitachi (JP); Hidehiro Minashima, Kodaira (JP); Yuzaburo Yano, Kodaira (JP); Noriaki Shiina, Osaka (JP); Kazuhiro Kodama, Osaka (JP); Mifuyu Ueno, Osaka (JP); Takashi Sato, Osaka (JP); Shinya Nakashima, Osaka (JP); Masaki Abe, Osaka (JP)

(73) Assignee: OTSUKA CHEMICAL CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/312,768

(22) PCT Filed: May 22, 2015

(86) PCT No.: PCT/JP2015/002596
§ 371 (c)(1),
(2) Date: Nov. 21, 2016

(87) PCT Pub. No.: WO2015/178037
PCT Pub. Date: Nov. 26, 2015

(65) Prior Publication Data
US 2017/0137604 A1    May 18, 2017

(30) Foreign Application Priority Data
May 22, 2014  (JP) .................. 2014-106393

(51) Int. Cl.
| | |
|---|---|
| C08K 5/18 | (2006.01) |
| C07C 211/55 | (2006.01) |
| B60C 1/00 | (2006.01) |
| C07C 211/51 | (2006.01) |
| C07C 237/04 | (2006.01) |
| C08K 5/20 | (2006.01) |
| C08L 9/00 | (2006.01) |
| C08L 7/00 | (2006.01) |
| C07C 211/53 | (2006.01) |

(52) U.S. Cl.
CPC .............. *C08K 5/18* (2013.01); *B60C 1/0016* (2013.01); *B60C 1/0025* (2013.01); *C07C 211/51* (2013.01); *C07C 211/53* (2013.01); *C07C 211/55* (2013.01); *C07C 237/04* (2013.01); *C08K 5/20* (2013.01); *C08L 7/00* (2013.01); *C08L 9/00* (2013.01)

(58) Field of Classification Search
CPC ........ C08K 5/18; C07C 211/53; C07C 211/55
See application file for complete search history.

(56) References Cited

U.S. PATENT DOCUMENTS

| | | | | |
|---|---|---|---|---|
| 2,705,224 A | * | 3/1955 | Hill ..................... | C08K 5/18 524/255 |
| 2,939,861 A | * | 6/1960 | Ambelang ............... | C08K 5/18 523/315 |
| 2,939,867 A | | 6/1960 | Ambelang | |

(Continued)

FOREIGN PATENT DOCUMENTS

| | | |
|---|---|---|
| CN | 103059355 A | 4/2013 |
| EP | 2604650 A1 | 6/2013 |
| GB | 835826 A | 5/1960 |
| JP | H0892370 A | 4/1996 |
| JP | 2005232355 A | 9/2005 |
| JP | 2010509415 A | 3/2010 |
| JP | 2010536952 A | 12/2010 |
| JP | 2013155259 A | 8/2013 |
| KR | 20020089891 A | 11/2002 |
| KR | 101392733 B1 | 5/2014 |

OTHER PUBLICATIONS

Nov. 22, 2016, International Preliminary Report on Patentability issued in the International Patent Application No. PCT/JP2015/002596.

(Continued)

*Primary Examiner* — Vickey M Nerangis
(74) *Attorney, Agent, or Firm* — Kenja IP Law PC

(57) ABSTRACT

Provided is a rubber composition that has better weather resistance than conventional rubber compositions and can inhibit rubber article surface discoloration. The rubber composition contains at least one rubber component selected from natural rubber and diene-based synthetic rubbers and, blended therewith, at least one bisphenyldiamine compound represented by formula (I). In formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1.

(I)

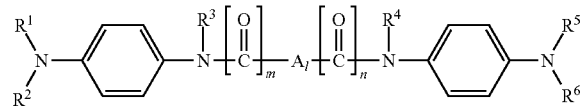

7 Claims, No Drawings

(56) References Cited

U.S. PATENT DOCUMENTS

| | | |
|---|---|---|
| 3,266,982 A | 8/1966 | Popoff |
| 3,396,005 A | 8/1968 | Popoff |
| 2005/0051248 A1 | 3/2005 | Hotaka et al. |

OTHER PUBLICATIONS

Jun. 30, 2015, International Search Report issued in the International Patent Application No. PCT/JP2015/002596.

Feb. 6, 2018, Notification of Reasons for Refusal issued by the Japan Patent Office in the corresponding Japanese Patent Application No. 2014-106393.

Michal Zalibera et al., "Monotrimethylene-Bridged Bis-p-phenylenediamine Radical Cations and Dications: Spin States, Conformations, and Dynamics", The Journal of Physical Chemistry A, Jan. 23, 2013, pp. 1439-1448, vol. 117, No. 7, American Chemical Society.

Nov. 14, 2017, Office Action issued by the State Intellectual Property Office in the corresponding Chinese Patent Application No. 201580026337.2.

Nov. 22, 2017, Extended European Search Report issued by the European Patent Office in the corresponding European Patent Application No. 15796606.0.

S. F. Torf et al., "Synthesis of Bisquaternary Ammonium Derivatives of Diphenyldiaminopropane Possessing Curare Like Action", Khimiko-Farmatsevticheskii Zhurnal, Jun. 6, 1972, pp. 22-25, vol. 7, No. 9.

Apr. 24, 2018, Notification of Reasons for Refusal issued by the Japan Patent Office in the corresponding Japanese Patent Application No. 2014-106393.

Viktor V. Jarikov et al., Photochemistry and Photophysics of Triarylmethane Dye Leuconitriles, The Journal of Organic Chemistry, Jan. 9, 2001, pp. 659-671, vol. 66, Issue 3, American Chemical Society.

* cited by examiner

RUBBER COMPOSITION, TIRE, BISPHENYLDIAMINE COMPOUND, AND ANTI-AGING AGENT

TECHNICAL FIELD

The present disclosure relates to a rubber composition, a tire, a bisphenyldiamine compound, and an anti-aging agent, and, in particular, relates to a rubber composition that is suitable for use in tread rubber or sidewall rubber of a tire.

BACKGROUND

Rubber articles having natural rubber or a diene-based synthetic rubber as a raw material generally deteriorate over time and suffer from crack formation at the surface thereof when exposed to an environment in which ozone is present. Such cracks propagate as the rubber article is subjected to static stress and dynamic stress, and may eventually result in rupturing of the rubber article.

In order to prevent and inhibit the formation and propagation of cracks in a rubber article due to ozone, particularly in the case of tread rubber or sidewall rubber of a tire, it has become common practice to use a rubber composition that contains an anti-aging agent in the form of an amine-based anti-aging agent such as N-(1,3-dimethylbutyl)-N'-phenyl-p-phenylenediamine (PTL 1 and 2).

CITATION LIST

Patent Literature

PTL 1: JP 2010-509415 A
PTL 2: JP 2010-536952 A

SUMMARY

Technical Problem

However, when an amine-based anti-aging agent such as described above is used in a rubber article, the external appearance of the rubber article may deteriorate as a consequence of the anti-aging agent having a high tendency to migrate to the surface of the rubber over time, leading to discoloration and staining of the rubber surface by what is referred to as "blooming".

In recent years, there has been demand for improvement of rubber article weather resistance, such as ozone resistance. Particularly in the case of tire production, strategies are being adopted for reducing the gauge thickness of various tire members in order to provide better fuel efficiency and conserve resources. Under these circumstances, there is demand for a rubber composition that has even better weather resistance than a conventional rubber composition containing an amine-based anti-aging agent such as described above.

Therefore, one objective of the present disclosure is to provide a rubber composition that has better weather resistance than conventional rubber compositions and can inhibit surface discoloration of a rubber article. Another objective of the present disclosure is to provide a tire that has superior weather resistance and in which rubber article surface discoloration is inhibited.

Solution to Problem

The inventors conducted diligent investigation in order to achieve the objectives described above, resulting in the discovery that a rubber composition that has superior weather resistance and that can inhibit surface discoloration of a rubber article can be obtained through blending of a compound having a specific structure with a rubber component. This discovery led to the present disclosure.

Specifically, a presently disclosed rubber composition comprises at least one rubber component selected from natural rubber and diene-based synthetic rubbers and, blended therewith, at least one bisphenyldiamine compound represented by formula (I) shown below

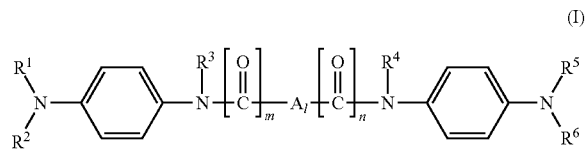

where, in formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1. As a result of the presently disclosed rubber composition containing the aforementioned bisphenyldiamine compound as an anti-aging agent, weather resistance of the presently disclosed rubber composition can be significantly improved compared to conventional rubber compositions and surface discoloration of a rubber article can be inhibited.

From a viewpoint of sufficiently improving weather resistance and preventing discoloration, it is preferable that in the bisphenyldiamine compound represented by formula (I) that is contained in the presently disclosed rubber composition as an anti-aging agent, one of $R^1$ and $R^2$ is a hydrogen atom, one of $R^5$ and $R^6$ is a hydrogen atom, $R^3$ and $R^4$ are each an alkyl group having a carbon number of 1-8, A is an alkylene group having a carbon number of 1-8, l is 1, and m and n are each 0.

In the presently disclosed rubber composition, a blending amount of the bisphenyldiamine compound represented by formula (I) is preferably in a range of from 0.2 parts by mass to 10 parts by mass relative to 100 parts by mass of the rubber component. As a result of the blending amount of the bisphenyldiamine compound being in the range described above, it is possible to sufficiently improve weather resistance and inhibit discoloration while also restricting the amount of the bisphenyldiamine compound that is consumed.

A presently disclosed tire comprises a tire member in which the above-described rubber composition is used. The aforementioned tire member is preferably either or both of a tread and a sidewall. The presently disclosed tire has superior weather resistance and rubber article surface discoloration is inhibited therein.

A presently disclosed bisphenyldiamine compound is represented by formula (I) shown below

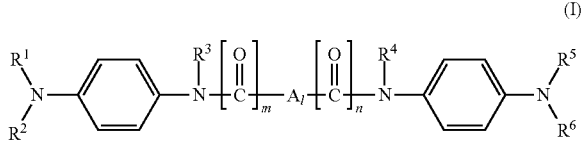

(I)

where, in formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1. A presently disclosed anti-aging agent for natural rubber and diene-based synthetic rubber-use comprises the above-described bisphenyldiamine compound.

Advantageous Effect

According to the present disclosure, it is possible to provide a rubber composition that has better weather resistance than conventional rubber compositions and that can inhibit surface discoloration of a rubber article, and also to provide a tire that has superior weather resistance and in which rubber article surface discoloration is inhibited.

DETAILED DESCRIPTION

<Rubber Composition>

The following provides a detailed description of the present disclosure. A presently disclosed rubber composition contains at least one rubber component selected from natural rubber and diene-based synthetic rubbers and, blended therewith, at least one bisphenyldiamine compound represented by formula (I) shown above.

<<Rubber Component>>

Examples of rubber components that can be used in the presently disclosed rubber composition include natural rubber (NR) and diene-based synthetic rubbers such as isoprene rubber (IR), butadiene rubber (BR), and styrene-butadiene copolymer rubber (SBR). One of these rubber components may be used individually, or two or more of these rubber components may be used in combination as necessary.

<<Bisphenyldiamine Compound>>

The presently disclosed rubber composition contains at least one bisphenyldiamine compound represented by formula (I) shown above. In formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1.

The bisphenyldiamine compound represented by formula (I) that is used in the presently disclosed rubber composition has a high molecular weight compared to conventional anti-aging agents and, as shown in formula (I), includes a bridge moiety having a characteristic and comparatively long chain length section. Specifically, the bisphenyldiamine compound represented by formula (I) includes a moiety represented by formula (II) shown below.

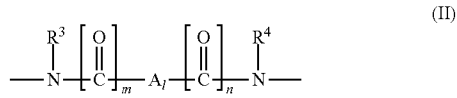

(II)

It is thought that as a result of the bisphenyldiamine compound having a high molecular weight and including this characteristic bridge moiety, the rate of diffusion of the bisphenyldiamine compound within the rubber composition is reduced and, accordingly, migration of the bisphenyldiamine compound to the rubber surface is inhibited to a greater extent.

The bisphenyldiamine compound represented by formula (I) has an excellent anti-aging effect with respect to rubber components such as natural rubber and diene-based synthetic rubbers, and can be used as an anti-aging agent for rubber component-use.

The following provides a description of the various chemical groups referred to in the present specification.

Examples of alkyl groups having a carbon number of 1-4 include linear, branched, and cyclic alkyl groups having a carbon number of 1-4 such as a methyl group, an ethyl group, an n-propyl group, an isopropyl group, an n-butyl group, an isobutyl group, a sec-butyl group, a tert-butyl group, and a cyclobutyl group.

Examples of alkyl groups having a carbon number of 1-8 include the examples of alkyl groups having a carbon number of 1-4 provided above and other linear, branched, and cyclic alkyl groups having a carbon number of 1-8 such as various pentyl groups, examples of which include an n-pentyl group, an isopentyl group, a neopentyl group, a tert-pentyl group, and a cyclopentyl group; various hexyl groups, examples of which include an n-hexyl group, an isohexyl group, a 4-methyl-2-pentyl group, and a cyclohexyl group; various heptyl groups, examples of which include an n-heptyl group and a 4-heptyl group; and various octyl groups, examples of which include an n-octyl group, an isooctyl group, and a 2-ethylhexyl group.

Examples of alkyl groups having a carbon number of 1-10 include the examples of alkyl groups having a carbon number of 1-8 provided above and other linear, branched, and cyclic alkyl groups having a carbon number of 1-10 such as various nonyl groups, examples of which include an n-nonyl group, a 3-ethylheptyl group, and a 4-methyloctyl group; and various decyl groups, examples of which include an n-decyl group and a 4-ethyloctyl group.

Examples of aralkyl groups include a benzyl group and a phenethyl group.

Examples of alkylene groups having a carbon number of 1 or 2 include a methylene group and an ethylene group.

Examples of alkylene groups having a carbon number of 1-4 include the examples of alkylene groups having a carbon number of 1 or 2 provided above and other linear and branched alkylene groups having a carbon number of 1-4 such as a trimethylene group, a propylene group, a dimethylmethylene group, a 2-methyltrimethylene group, and a tetramethylene group.

Examples of alkylene groups having a carbon number of 1-8 include the examples of alkylene groups having a carbon number 1-4 provided above and other linear and branched alkylene groups having a carbon number of 1-8 such as a pentamethylene group, a hexamethylene group, a 1,4-dimethyltetramethylene group, a heptamethylene group, and an octamethylene group.

Examples of alkylene groups having a carbon number of 1-10 include the examples of alkylene groups having a carbon number of 1-8 provided above and other linear and branched alkylene groups having a carbon number of 1-10 such as a nonamethylene group, a decamethylene group, and a 1,8-dimethyloctamethylene group.

Examples of alkylene groups having a carbon number of 1-12 include the examples of alkylene groups having a carbon number of 1-10 provided above and other linear and branched alkylene groups having a carbon number of 1-12 such as an undecamethylene group, a dodecamethylene group, and a 1,10-dimethyldecamethylene group.

In the bisphenyldiamine compound represented by formula (I), $R^1$, $R^2$, $R^5$, and $R^6$ are each, independently of one another, a hydrogen atom, an alkyl group having a carbon number of 1-10, or a phenyl group. However, from a viewpoint of sufficiently improving weather resistance and preventing discoloration, it is preferable that one of $R^1$ and $R^2$ is a hydrogen atom and that one of $R^5$ and $R^6$ is a hydrogen atom, and it is more preferable that one of $R^1$ and $R^2$ is a hydrogen atom and the other one of $R^1$ and $R^2$ is an alkyl group having a carbon number of 1-4, and that one of $R^5$ and $R^6$ is a hydrogen atom and the other one of $R^5$ and $R^6$ is an alkyl group having a carbon number of 1-4.

In the bisphenyldiamine compound represented by formula (I), $R^3$ and $R^4$ are each, independently of one another, an alkyl group having a carbon number of 1-8 or an aralkyl group. However, from a viewpoint of sufficiently improving weather resistance and preventing discoloration, $R^3$ and $R^4$ are preferably each an alkyl group having a carbon number of 1-8, more preferably each an alkyl group having a carbon number of 1-4, and particularly preferably each an alkyl group having a carbon number of 1-3.

In the bisphenyldiamine compound represented by formula (I), A is an alkylene group having a carbon number of 1-12. However, from a viewpoint of sufficiently improving weather resistance and preventing discoloration, A is preferably an alkylene group having a carbon number of 1-8, more preferably an alkylene group having a carbon number of 1-4, and particularly preferably an alkylene group having a carbon number of 1 or 2. The aforementioned alkylene group may be a linear, branched, or cyclic alkylene group.

In the bisphenyldiamine compound represented by formula (I), l, m, and n are each an integer of 0 or 1. However, from a viewpoint of sufficiently improving weather resistance and preventing discoloration, it is preferable that 1 is 1 and that m and n are each 0.

Examples of compounds such as described above include
N,N'-bis[4-(isopropylamino)phenyl]-N,N'-dimethylethane-1,2-diamine,
N,N'-diisopropyl-N,N'-bis[4-(isopropylamino)phenyl]ethane-1,2-diamine,
N,N'-diisopropyl-N,N'-bis[4-(pentan-3-ylamino)phenyl]ethane-1,2-diamine,
N,N'-dibenzyl-N,N'-bis[4-(pentan-3-ylamino)phenyl]ethane-1,2-diamine,
N,N'-bis[4-(diisopropylamino)phenyl]-N,N'-diisopropylethane-1,2-diamine,
N,N'-bis(4-anilinophenyl)-N,N'-diisopropyldecane-1,10-diamine,
N,N'-bis(4-anlinophenyl)-N,N'-bis(4-methylpentan-2-yl)oxamide,
N,N'-bis(4-anilinophenyl)-N,N'-bis(4-methylpentan-2-yl)adipamide,
N,N'-diethyl-N,N'-bis[4-(isopropylamino)phenyl]ethane-1,2-diamine,
N,N'-diisopropyl-N,N'-bis[4-(isopropylamino)phenyl]hexane-1,6-diamine,
N,N'-bis[4-(heptan-4-ylamino)phenyl]-N,N'-diisopropylethane-1,2-diamine,
N,N'-bis(4-anilinophenyl)-N,N'diisopropylpentane-1,5-diamine,
N,N'-bis(4-anilinophenyl)-N,N'-bis(4-methylpentan-2-yl)pentane-1,5-diamine,
and N,N'-bis(4-anilinophenyl)-N,N'-diisopropylhexane-1,6-diamine. Of these compounds,
N,N'-bis[4-(isopropylamino)phenyl]-N,N'-dimethylethane-1,2-diamine,
N,N'-diisopropyl-N,N'-bis[4-(isopropylamino)phenyl]ethane-1,2-diamine,
N,N'-diisopropyl-N,N'-bis[4-(pentan-3-ylamino)phenyl]ethane-1,2-diamine,
N,N'-bis(4-anilinophenyl)-N,N'diisopropyldecane-1,10-diamine,
N,N'-diethyl-N,N'-bis[4-(isopropylamino)phenyl]ethane-1,2-diamine,
N,N'-diisopropyl-N,N'-bis[4-(isopropylamino)phenyl]hexane-1,6-diamine,
and N,N'-bis(4-anilinophenyl)-N,N'-diisopropylhexane-1,6-diamine are preferable.

The bisphenyldiamine compound represented by formula (I) can be produced through reactions represented by reaction formulae 1-4 shown below.

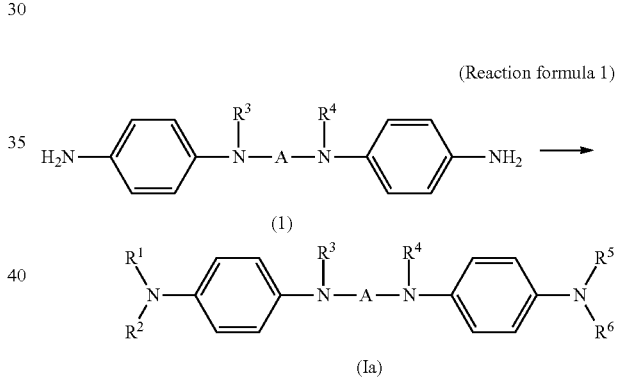

(Reaction formula 1)

(In reaction formula 1, $R^1$, $R^2$, $R^3$, $R^4$, $R^5$, $R^6$, and A are the same as previously described.)

According to reaction formula 1, a bisphenyldiamine compound represented by formula (Ia) can be produced through alkylation or aralkylation of amino groups of an aniline compound represented by formula (1). The bisphenyldiamine compound represented by formula (Ia) is a compound that is included within the scope of the presently disclosed bisphenyldiamine compound represented by formula (I).

The alkylation reaction or aralkylation reaction of amino groups of the aniline compound represented by formula (1) can for example be a reductive amination reaction in which a ketone or aldehyde is caused to act on the aniline compound represented by formula (1) in the presence of a reducing agent or through a catalytic hydrogen reduction reaction in the presence of a metal catalyst.

A reductive amination reaction in which a ketone or aldehyde is caused to act on the aniline compound represented by formula (1) in the presence of a reducing agent is carried out in a solvent that may be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, particularly in the case of a borohydride reducing agent, alcohol solvents such as methanol, ethanol, n-propanol, isopropyl alcohol, and n-butanol. One of these solvents may be used individually, or a mixture of two or more of these solvents may be used as necessary.

The amount of such solvents that is used relative to 1 part by mass of the aniline compound represented by formula (1) is normally approximately 1 part by mass to 500 parts by mass and preferably approximately 5 parts by mass to 100 parts by mass.

Examples of reducing agents that can be used in the reaction include lithium aluminum hydride, sodium borohydride, lithium borohydride, sodium cyanoborohydride, and lithium triethylborohydride.

The amount of such reducing agents that is used relative to the aniline compound represented by formula (1) is normally from 0.5 equivalents to 10 equivalents, preferably from 0.5 equivalents to 2.0 equivalents, and more preferably from 0.5 equivalents to 1.0 equivalents.

Examples of the ketone or aldehyde used in the reaction include linear, branched, and cyclic aldehyde compounds having a carbon number of 1-10 such as formaldehyde, acetaldehyde, propanal, butanal, isobutyraldehyde, hexanal, nonanal, decanal, benzaldehyde, and phenylacetaldehyde; and linear, branched, and cyclic ketone compounds having a carbon number of 1-10 such as acetone, methyl ethyl ketone, diethyl ketone, cyclohexanone, methyl isobutyl ketone, and acetophenone.

The amount of the ketone or aldehyde that is used in the reaction is normally from 2.0 equivalents to 10.0 equivalents, preferably from 2.0 equivalents to 5.0 equivalents, and more preferably from 2.0 equivalents to 2.2 equivalents.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

A reductive amination reaction in which a ketone or aldehyde is caused to act on the aniline compound represented by formula (1) through a catalytic hydrogen reduction reaction in the presence of a metal catalyst is preferably carried out in a solvent. The solvent may be selected from a wide range of commonly known solvents that are inert with respect to the reaction, examples of which include alcohol solvents such as methanol, ethanol, n-propanol, isopropyl alcohol, and n-butanol; organic acids such as acetic acid and propionic acid; hydrocarbon solvents such as cyclohexane; and ether solvents such as tetrahydrofuran. One of these solvents may be used individually, or a mixture of two or more of these solvents may be used as necessary.

The amount of such solvents that is used relative to 1 part by mass of the aniline compound represented by formula (1) is normally approximately 1 part by mass to 500 parts by mass and preferably approximately 1 part by mass to 20 parts by mass.

Examples of metal catalysts that can be used include palladium on carbon, platinum black (platinum on carbon), sulfided platinum on carbon, platinum oxide, Raney nickel, and Raney cobalt.

The amount of such metal catalysts that is used relative to 1 part by mass of the aniline compound represented by formula (1) is normally from 0.0001 parts by mass to 0.5 parts by mass, preferably from 0.0001 parts by mass to 0.1 parts by mass, and more preferably from 0.0001 parts by mass to 0.01 parts by mass.

The reaction can normally be carried out in a temperature range of from −78° C. to the boiling temperature of the solvent that is used. However, the reaction is normally carried out at approximately −10° C. to 50° C. and preferably at around room temperature.

The reaction is carried out under a hydrogen atmosphere at a pressure that is normally from atmospheric pressure to 10 MPa, preferably from atmospheric pressure to 1.0 MPa, and more preferably around atmospheric pressure.

Although it is not possible to make generalizations about the reaction time since the reaction time varies depending on the reaction temperature and so forth, the reaction is normally completed in approximately 0.5 hours to 24 hours.

(Reaction formula 2)

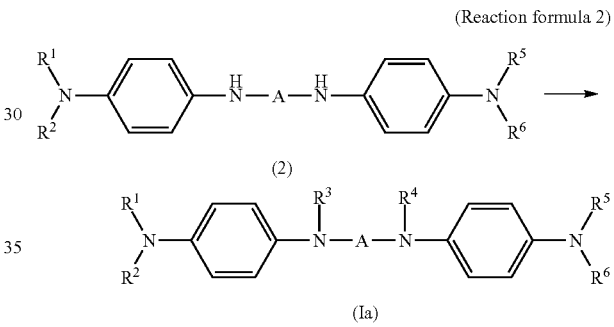

(In reaction formula 2, $R^1$, $R^2$, $R^3$, $R^4$, $R^5$, $R^6$ and A are the same as previously described.)

According to reaction formula 2, the bisphenyldiamine compound represented by formula (Ia) can be produced through alkylation or aralkylation of amino groups of an amino compound represented by formula (2).

The alkylation reaction or aralkylation reaction of the amino groups of the amino compound represented by formula (2) can for example be carried out by a method in which an alkyl halide having a carbon number of 1-8 or an aralkyl halide is caused to act on the amino compound represented by formula (2).

The reaction is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; aromatic solvents such as toluene, xylene, and benzene; halogen-containing solvents such as dichloromethane and carbon tetrachloride; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the amino compound represented by formula (2)

is normally approximately 1 part by mass to 500 parts by mass and preferably approximately 5 parts by mass to 100 parts by mass.

Furthermore, a base may be used in the reaction. Examples of bases that can be used include tertiary alkyl amines such as triethylamine and diisopropylethylamine; hydrides such as lithium hydride, sodium hydride, and potassium hydride; alkyllithiums such as methyllithium, ethyllithium, n-butyllithium, and tert-butyllithium; amine metal salts such as lithium diisopropylamide, lithium hexamethyldisilazide, and sodium hexamethyldisilazide; and caustic compounds such as sodium hydroxide and potassium hydroxide.

The amount of such bases that is used relative to the amino compound represented by formula (2) is normally from 2.0 equivalents to 10.0 equivalents, preferably from 2.0 equivalents to 5.0 equivalents, and more preferably from 2.0 equivalents to 2.2 equivalents.

The amount of the alkyl halide or aralkyl halide that is used in the reaction is normally from 2.0 equivalents to 10.0 equivalents, preferably from 2.0 equivalents to 5.0 equivalents, and more preferably from 2.0 equivalents to 2.2 equivalents.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

Alternatively, instead of this method involving the action an alkyl halide or aralkyl halide, a reductive amination reaction involving the action of an aldehyde or ketone in the presence of a reducing agent may be adopted.

In such a situation, the reaction conditions and so forth can be in accordance with those of reaction formula 1.

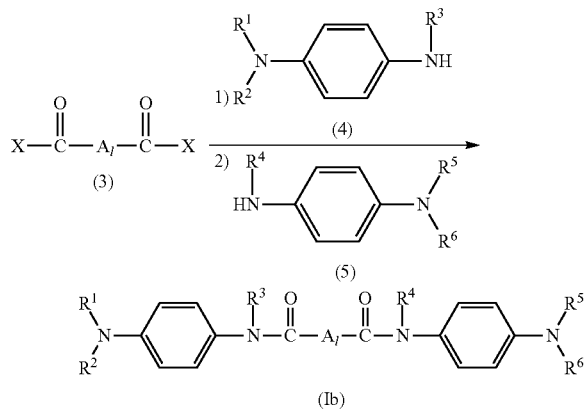

(Reaction formula 3)

(In reaction formula 3, $R^1$, $R^2$, $R^3$, $R^4$, $R^5$, $R^6$, A, and l are the same as previously described, and X represents a halogen atom.)

According to reaction formula 3, a bisphenyldiamine compound represented by formula (Ib) can be produced by causing a carboxylic acid halide represented by formula (3) to act on a phenylamine compound represented by formula (4), and subsequently on a phenylamine compound represented by formula (5). The bisphenyldiamine compound represented by formula (Ib) is a compound that is included within the scope of the presently disclosed bisphenyldiamine compound represented by formula (I).

The reaction is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; aromatic solvents such as toluene, xylene, and benzene; halogen-containing solvents such as dichloromethane and carbon tetrachloride; amide solvents such as N,N-dimethylformamide, N,N-dimethylacetamide, and hexamethylphosphoric triamide; and sulfoxide solvents such as dimethyl sulfoxide. One of these solvents may be used individually, or a mixture of two or more of these solvents may be used as necessary.

The amount of such solvents that is used relative to 1 part by mass of the phenylamine compound represented by formula (4) or the phenylamine compound represented by formula (5) is normally approximately 1 part by mass to 500 parts by mass and preferably approximately 5 parts by mass to 100 parts by mass.

The amount of the phenylamine compound represented by formula (4) or the phenylamine compound represented by formula (5) that is used in the reaction relative to the carboxylic acid halide represented by formula (3) is normally from 2.0 equivalents to 10.0 equivalents, preferably from 2.0 equivalents to 5.0 equivalents, and more preferably from 2.0 equivalents to 2.2 equivalents.

The reaction is preferably carried out in the presence of a base. Examples of bases that can be used include aromatic amines such as pyridine, N,N-dimethyl-4-aminopyridine, pyrazine, and 2,6-lutidine; tertiary aliphatic amines such as trimethylamine, triethylamine, diisopropylethylamine, and N-methylpyrrolidine; and caustic compounds such as sodium hydroxide and potassium hydroxide. The amount of such bases that is used relative to the amino compound represented by formula (2) is normally from 2.0 equivalents to 10.0 equivalents, preferably from 2.0 equivalents to 5.0 equivalents, and more preferably from 2.0 equivalents to 2.2 equivalents.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

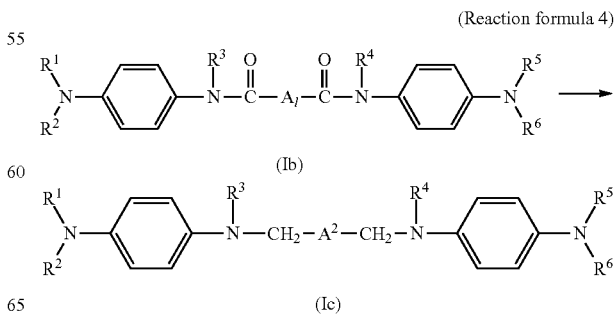

(Reaction formula 4)

(In reaction formula 4, $R^1$, $R^2$, $R^3$, $R^4$, $R^5$, $R^6$, A, and 1 are the same as previously described, and $A^2$ represents an alkylene group having a carbon number of 1-10.)

According to reaction formula 4, a bisphenyldiamine compound represented by formula (Ic) can be produced by using a reducing agent in order to reduce carbonyl groups of the bisphenyldiamine compound represented by formula (Ib), which is produced in the previously described reaction formula 3. The bisphenyldiamine compound represented by formula (Ic) is a compound that is included within the scope of the presently disclosed bisphenyldiamine compound represented by formula (I).

The reaction is carried out in a solvent that can be selected from a wide range of commonly known solvents that are inert with respect to the reaction. Examples of solvents that can be used include ether solvents such as dimethyl ether, diethyl ether, diisopropyl ether, tert-butyl methyl ether, tetrahydrofuran, dioxane, tetrahydropyran, and 1,2-dimethoxyethane; halogen-containing solvents such as dichloromethane and carbon tetrachloride; and, in the case of a borohydride reducing agent, alcohol solvents such as methanol, ethanol, n-propanol, isopropyl alcohol, and n-butanol.

One of these solvents may be used individually, or a mixture of two or more of these solvents may be used as necessary.

The amount of such solvents that is used relative to 1 part by mass of the aniline compound represented by formula (1) is normally approximately 1 part by mass to 500 parts by mass and preferably approximately 5 parts by mass to 100 parts by mass.

Examples of reducing agents that can be used in the reaction include lithium aluminum hydride, sodium borohydride, borane, and diborane. Furthermore, lithium aluminum hydride may be used in combination with aluminum chloride, or sodium borohydride may be used in combination with a Lewis acid such as tin tetrachloride or boron trifluoride diethyl ether complex.

The amount of such reducing agents that is used relative to the bisphenyldiamine compound represented by formula (Ib) is normally from 1.5 equivalents to 20.0 equivalents, preferably from 1.5 equivalents to 6.0 equivalents, and more preferably 1.5 equivalents.

The reaction can normally be carried out in a temperature range of from −78° C. to the boiling temperature of the solvent that is used. However, the reaction is normally carried out at approximately −10° C. to 50° C. and preferably at around room temperature.

Although it is not possible to make generalizations about the reaction time since the reaction time varies depending on the reaction temperature and so forth, the reaction is normally completed in approximately 0.5 hours to 24 hours.

The aniline compound represented by formula (1) and the amino compound represented by formula (2) that are used in previously described reaction formulae 1 and 2 can be produced by the methods shown below in reaction formulae 5 and 6.

(Reaction formula 5)

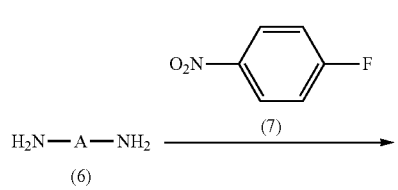

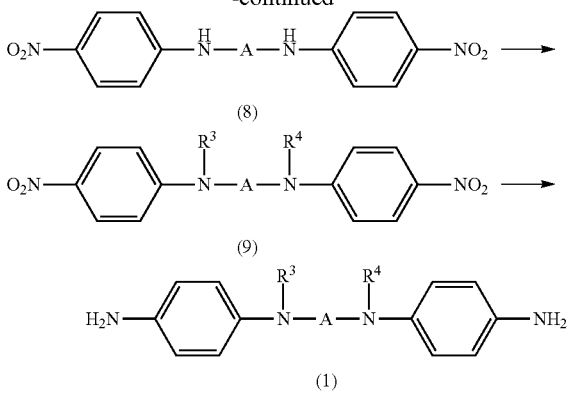

(In reaction formula 5, $R^3$, $R^4$, and A are the same as previously described.)

According to reaction formula 5, 4-fluoronitrobenzene represented by formula (7) is first caused to react with a diamine compound represented by formula (6) in the presence of a base such as potassium carbonate to produce a bisnitrophenyldiamine compound represented by formula (8). The resultant bisnitrophenyldiamine compound represented by formula (8) is subsequently subjected to an alkylation reaction or aralkylation reaction to produce a substituted amine compound represented by formula (9). The alkylation reaction or aralkylation reaction may be carried out in accordance with the reaction shown in the previously described reaction formula 2. The aniline compound represented by formula (1) can then be produced by reducing nitro groups of the resultant substituted amine compound represented by formula (9). The reaction can be carried out under reaction conditions that are commonly known for formation of an amino group through reduction of a nitro group on a benzene ring.

(Reaction formula 6)

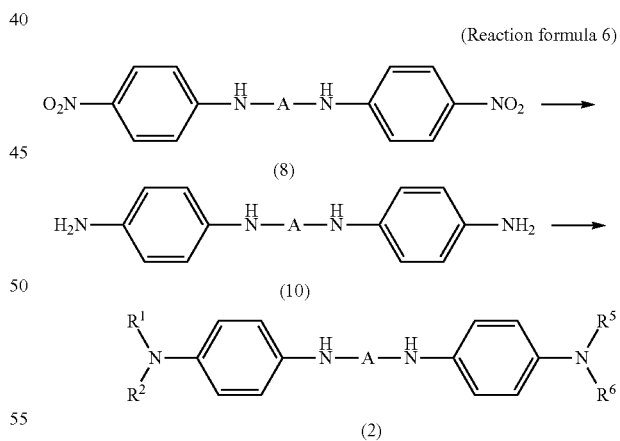

(In reaction formula 6, $R^1$, $R^2$, $R^5$, $R^6$, and A are the same as previously described.)

According to reaction formula 6, nitro groups on benzene rings of the bisnitrophenyldiamine compound represented by formula (8), which is produced in reaction formula 5, are reduced under commonly known reaction conditions to produce an aniline compound represented by formula (10). Thereafter, the amino compound represented by formula (2) can be produced by carrying out an alkylation reaction or aralkylation reaction with respect to amino groups of the aniline compound represented by formula (10). The alkylation reaction or aralkylation reaction of the amino groups may be carried out in accordance with the reaction shown in the previously described reaction formula 1.

In a situation in which the bisphenyldiamine compound represented by formula (I) is used as an anti-aging agent, the blending amount of the bisphenyldiamine compound relative to 100 parts by mass of the rubber component is preferably in a range of from 0.2 parts by mass to 10 parts by mass and more preferably in a range of from 0.5 parts by mass to 7.5 parts by mass. As a result of the blending amount of the anti-aging agent represented by formula (I) being at least 0.2 parts by mass relative to 100 parts by mass of the rubber component, weather resistance of the rubber composition, such as ozone resistance, can be sufficiently improved and surface discoloration of a rubber article can be effectively inhibited. On the other hand, it is advantageous in terms of raw material costs of the rubber composition for the blending amount of the bisphenyldiamine compound represented by formula (I) to be no greater than 10 parts by mass relative to 100 parts by mass of the rubber component since this enables the amount of the bisphenyldiamine compound represented by formula (I) that is consumed as the anti-aging agent to be restricted while sufficiently improving weather resistance and inhibiting discoloration.

It should be noted that the presently disclosed rubber composition may contain the bisphenyldiamine compound represented by formula (I) in combination with another anti-aging agent such as an amine-based anti-aging agent. In such a situation, the blending amount of the anti-aging agent other than the bisphenyldiamine compound represented by formula (I) is preferably in a range of from 0 parts by mass to 5 parts by mass relative to 100 parts by mass of the rubber component.

<<Other Components>>

The presently disclosed rubber composition may contain carbon black, silica, or the like as a reinforcing filler. No specific limitations are placed on the carbon black that is used. Likewise, the silica can be any commercially available silica, among which, wet silica, dry silica, and colloidal silica are preferable, and wet silica is more preferable. The blending amount of the reinforcing filler is preferably in a range of from 5 parts by mass to 200 parts by mass relative to 100 parts by mass of the rubber component. In a situation in which silica is used as a reinforcing filler, it is preferable that a silane coupling agent is contained in an amount of approximately 1 mass % to 20 mass % relative to the silica from a viewpoint of reinforcing properties and it is more preferable that the silane coupling agent is contained in a range of from 6 mass % to 12 mass % from a viewpoint of heat-generation properties.

The presently disclosed rubber composition may further contain compounding agents commonly used in the rubber industry that are appropriately selected so as not to impair the objectives of the present disclosure. Examples of such compounding agents include vulcanizing agents, vulcanization accelerators, anti-scorch agents, softeners, zinc oxide, and stearic acid. Commercially available products may be suitably used as the compounding agents. The rubber composition can be produced by kneading, warming, extrusion, and the like of the rubber component, the bisphenyldiamine compound represented by formula (I), and various compounding agents that are appropriately selected as necessary.

<Tire>

A presently disclosed tire includes at least one tire member in which the above-described rubber composition is used. A tread and a sidewall that are exposed at the outer surface are preferable examples of the aforementioned tire member. Through use of the above-described rubber composition, the presently disclosed tire benefits from superior weather resistance and inhibition of rubber article surface discoloration.

EXAMPLES

The following provides a more detailed explanation of the present disclosure through examples and production examples. However, the present disclosure is not in any way limited by the following examples.

Production Example 1

Production of N,N'-bis[4-(isopropylamino)phenyl]-N,N'-dimethylethane-1,2-diamine (compound I-1)

(1) Production of N,N'-bis(4-nitrophenyl)ethane-1,2-diamine

After 4.79 g of ethylenediamine and 73.3 g of potassium carbonate had been added to a solution of 25.0 g of 4-fluoronitrobenzene in 150 mL of N,N-dimethylformamide, the solution was stirred overnight at 100° C. The resultant reaction liquid was filtered using Celite and, after 500 mL of water and 300 mL of ethyl acetate had been added to the filtrate, liquid separation was performed to obtain an organic layer. The organic layer was concentrated under reduced pressure to obtain a solid residue that was subsequently washed with a mixed liquid of isopropyl alcohol and diisopropyl ether and dried under reduced pressure to yield 21.3 g (88% yield) of N,N'-bis(4-nitrophenyl)ethane-1,2-diamine.

(2) Production of N,N'-bis(4-nitrophenyl)-N,N'-dimethylethane-1,2-diamine

A solution of 100 g of N,N'-bis(4-nitrophenyl)ethane-1,2-diamine, produced according to the description in section (1), in 800 mL of N,N-dimethylformamide was ice cooled and, after 48 g of sodium hydride (60% oil suspension) had been added thereto, was returned to room temperature and stirred for 1 hour. The resultant solution was ice cooled once again and, after 128.7 g of methyl iodide had been dripped therein, was stirred for 13 hours at room temperature. The resultant reaction liquid was added to 2,000 mL of water, was stirred for 1 hour, and was then filtered to obtain a solid. The solid was crushed and washed with water and methanol in this order, and was dried under reduced pressure to yield 109 g (99% yield) of N,N'-bis(4-nitrophenyl)-N,N'-dimethyl ethane-1,2-diamine.

(3) Production of N,N'-bis(4-aminophenyl)-N,N'-dimethylethane-1,2-diamine

After 2 g of 5% palladium on carbon had been added to a methanol suspension of 109 g of N,N'-bi s(4-nitrophenyl)-N,N'-dimethyl ethane-1,2-diamine, the methanol suspension was stirred for 3 days at 50° C. under a hydrogen atmosphere. The resultant reaction liquid was filtered and the filtrate was concentrated under reduced pressure to obtain a solid residue. The solid residue was washed with ethyl acetate and dried under reduced pressure to yield 87 g (97% yield) of N,N'-bi s(4-aminophenyl)-N,N'-dimethylethane-1,2-diamine.

(4) Production of N,N'-bis[4-(isopropylamino)phenyl]-N,N'-dimethylethane-1,2-diamine (compound I-1)

After 14.1 g of acetone had been added to a solution of 30.0 g of N,N'-bis(4-aminophenyl)-N,N'-dimethylethane-1,2-diamine in 250 mL of methanol, the solution was ice cooled and 15.3 g of sodium cyanoborohydride was added thereto. The solution was adjusted to a pH of 6.5-7.5 using acetic acid, and was then returned to room temperature and stirred for 3 hours. The resultant reaction liquid was concentrated under reduced pressure to obtain a residue. Thereafter, 320 mL of 1N sodium hydroxide aqueous solution was added to the residue and stirring was performed for 1 hour at room temperature. After 300 mL of ethyl acetate had been added to the reaction liquid, liquid separation was carried out to obtain an organic layer. The organic layer was washed with 100 mL of water and concentrated under reduced pressure, and the resultant residue was dissolved in chloroform and processed by silica gel column chromatography (hexane:ethyl acetate=3:2 →1:1). Ice-cooled hexane was added to the resultant orange oil. Thereafter, precipitated solid was filtered off and was dried under reduced pressure to yield 34.6 g (88% yield) of N,N'-bis[4-(isopropylamino)phenyl]-N,N'-dimethylethane-1,2-diamine (compound I-1) represented by the following formula.

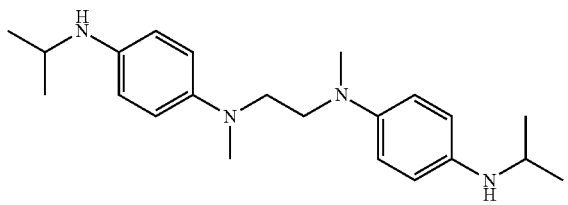

(I-1)

Properties: Yellow solid
Melting point: 71° C.
$^1$H-NMR (300 MHz, CDCl$_3$, δ ppm): 1.18 (d, 12H), 2.86 (s, 6H), 3.35 (s, 4H), 3.53 (dq, 2H), 6.58 (d, 4H), 6.65 (d, 4H)

Production Example 2

Production of N,N'-diisopropyl-N,N'-bis[4-(isopropylamino)phenyl]ethane-1,2-diamine (compound I-2)

(1) Production of N,N'-bis(4-nitrophenyl)ethane-1,2-diamine

After 4.79 g of ethylenediamine and 73.3 g of potassium carbonate had been added to a solution of 25.0 g of 4-fluoronitrobenzene in 150 mL of N,N-dimethylformamide, the solution was stirred overnight at 100° C. The resultant reaction liquid was filtered using Celite and, after 500 mL of water and 300 mL of ethyl acetate had been added to the filtrate, liquid separation was performed to obtain an organic layer. The organic layer was concentrated under reduced pressure to obtain a solid residue that was subsequently washed with a mixed liquid of isopropyl alcohol and diisopropyl ether and dried under reduced pressure to yield 21.3 g (88% yield) of N,N'-bi s(4-nitrophenyl)ethane-1,2-diamine.

(2) Production of N,N'-bis(4-aminophenyl)ethane-1,2-diamine

After 400 mg of 5% palladium on carbon had been added to a methanol suspension of 11.9 g of N,N'-bis(4-nitrophenyl)ethane-1,2-diamine, the methanol suspension was stirred for 3 days at room temperature under a hydrogen atmosphere. The resultant reaction liquid was filtered and the filtrate was concentrated under reduced pressure to obtain a solid residue. The solid residue was washed with isopropyl alcohol and ethyl acetate, and was dried under reduced pressure to yield 7.36 g (77% yield) of N,N'-bis(4-aminophenyl)ethane-1,2-diamine as a brown solid.

(3) Production of N,N'-diisopropyl-N,N'-bis[4-(isopropylamino)phenyl]ethane-1,2-diamine (compound I-2)

After 9.12 mL of acetone had been added to a solution of 5.00 g of N,N'-bis(4-aminophenyl)ethane-1,2-diamine in 50 mL of methanol, the solution was ice cooled and 5.71 g of sodium cyanoborohydride was added thereto. Thereafter, the solution was adjusted to a pH of 6.5-7.5 using acetic acid and was then stirred for 3 hours at room temperature. The resultant reaction liquid was concentrated under reduced pressure to obtain a residue. Thereafter, 80 mL of 1N sodium hydroxide aqueous solution was added to the residue and stirring was performed for 1 hour at room temperature. After 70 mL of ethyl acetate had been added to the reaction liquid, liquid separation was carried out to obtain an organic layer. The organic layer was washed with 10 mL of water and concentrated under reduced pressure, and the resultant residue was dissolved in chloroform and processed by silica gel column chromatography (hexane:ethyl acetate=3:2). Ice-cooled hexane was added to the resultant orange oil. Thereafter, precipitated solid was filtered off and was dried under reduced pressure to yield 5.95 g (70% yield) of N,N'-diisopropyl-N,N'-bis[4-(isopropylamino)phenyl]ethane-1,2-diamine (compound I-2) represented by the following formula.

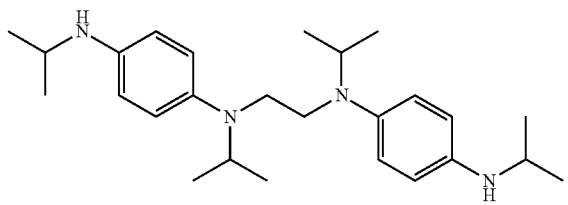

(I-2)

Properties: Yellow solid
Melting point: 81-82° C.
$^1$H-NMR (300 MHz, DMSO-D$_6$, δ ppm): 0.94 (d, 12H), 1.08 (d, 12H), 2.89 (s, 4H), 3.49 (m, 4H), 4.72 (br-s, 2H), 6.45 (m, 4H), 6.65 (m, 4H)

Production Example 3

Production of N,N'-diisopropyl-N,N'-bis[4-(pentan-3-ylamino)phenyl]ethane-1,2-diamine (compound I-3)

(1) Production of N,N'-bis[4-(pentan-3-ylamino)phenyl]ethane-1,2-diamine

After 23.5 g of diethyl ketone had been added to a solution of 30.0 g of N,N'-bis(4-aminophenyl)ethane-1,2-diamine in 300 mL of methanol, 17.1 g of sodium cyanoborohydride was added under ice cooling, and then 12 mL of acetic acid was added in two portions. Stirring was performed for 1.5 hours under ice cooling and then overnight at room temperature. Next, 250 mL of 1N sodium hydroxide aqueous solution was added to the reaction liquid and stirring was performed for 30 minutes. Thereafter, extraction was performed with chloroform and the resultant organic layer was washed once with water. The organic layer was concentrated under reduced pressure to obtain a residue that was then dissolved in chloroform, processed by silica gel column chromatography (hexane:ethyl acetate=3:2), and purified by once again being processed by silica gel column chromatography (hexane:ethyl acetate=1:1) to yield 28.5 g (60% yield) of N,N'-bis[4-(pentan-3-ylamino)phenyl]ethane-1,2-diamine as a dark brown solid.

(2) Production of N,N'-diisopropyl-N,N'-bis[4-(pentan-3-ylamino)phenyl]ethane-1,2-diamine (compound I-3)

After 17.3 g of acetone had been added to a solution of 28.5 g of N,N'-bis[4-(pentan-3-ylamino)phenyl]ethane-1,2-diamine in 300 mL of methanol, the solution was ice cooled and 10.3 g of sodium cyanoborohydride and 6.3 mL of acetic acid were added thereto. Stirring was performed for 2 hours at room temperature, after which, the reaction liquid was concentrated under reduced pressure to obtain a residue. Next, 126 mL of 1N sodium hydroxide aqueous solution was added to the residue and stirring was performed. Thereafter, extraction was performed using chloroform and the resultant organic layer was washed with water. The organic layer was concentrated under reduced pressure to obtain a residue that was then processed by silica gel column chromatography (hexane:ethyl acetate=3:2). The resultant crude crystals were washed with ice-cooled hexane to yield 24.5 g (70% yield) of N,N'-diisopropyl-N,N'-bis[4-(pentan-3-ylamino)phenyl]ethane-1,2-diamine (compound I-3) represented by the following formula.

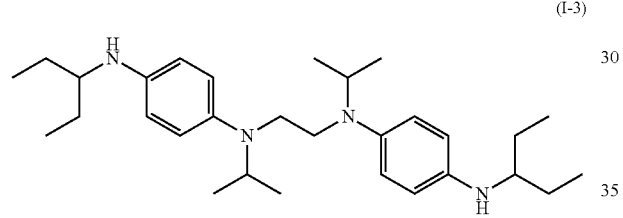

(I-3)

Properties: Beige solid
Melting point: 76° C.
$^1$H-NMR (300 MHz, DMSO-D$_6$, δ ppm): 0.86 (t, 12H), 0.96 (d, 12H), 1.41 (m, 8H), 2.90 (s, 4H), 3.05 (m, 2H), 4.69 (br-d, 2H), 6.47 (m, 4H), 6.66 (m, 4H)

Production Example 4

Production of N,N'-dibenzyl-N,N'-bis[4-(pentan-3-yl amino)phenyl]ethane-1,2-diamine (compound I-4)

(1) Production of N,N'-dibenzyl-N,N'-bis(4-nitrophenyl)ethane-1,2-diamine

After 7.94 g of sodium hydride (60% oil suspension) had been added to a solution of 25.0 g of N,N'-bis(4-nitrophenyl)ethane-1,2-diamine in 400 mL of N,N-dimethylformamide, the solution was stirred for 10 minutes under ice cooling. Stirring was performed for a further 2 hours at room temperature after addition of 23.6 mL of benzyl bromide. The resultant reaction liquid was ice cooled and, after methanol and water has been added thereto, was filtered to obtain a solid. The solid was washed with water, isopropyl ether, and hexane in this order and was dried under reduced pressure to yield 40.3 g (100% yield) of N,N'-dibenzyl-N,N'-bis(4-nitrophenyl)ethane-1,2-diamine as a yellow solid.

(2) Production of N,N'-dibenzyl-N,N'-bis(4-aminophenyl)ethane-1,2-diamine

After 2.0 g of 10% platinum on carbon had been added to a suspension of 20.0g of N,N'-dibenzyl-N,N'-bis(4-nitrophenyl)ethane-1,2-diamine in 500 mL of methanol, the suspension was stirred overnight under a hydrogen atmosphere. Further stirring under a hydrogen atmosphere was performed for 1 week after addition of 200 mL of 1,4-dioxane. The resultant reaction liquid was filtered and the filtrate was subsequently concentrated under reduced pressure. Precipitated solid was filtered off to yield 17.0 g (97% yield) of N,N'-dibenzyl-N,N'-bis(4-aminophenyl)ethane-1,2-diamine as a dark purple solid.

(3) Production of N,N'-dibenzyl-N,N'-bis[4-(pentan-3-ylamino)phenyl]ethane-1,2-diamine (compound I-4)

After 12.9 mL of diethyl ketone had been added to a solution of 20.7 g of N,N'-dibenzyl-N,N'-bis(4-aminophenyl)ethane-1,2-diamine, produced according to the description in section (2), in 200 mL of methanol, 6.5 g of sodium cyanoborohydride was further added under ice cooling. The solution was adjusted to a pH of 6.5-7.5 using acetic acid, was stirred for 20 minutes under ice cooling, and was subsequently returned to room temperature and stirred for 4 hours. Saturated sodium carbonate aqueous solution was added to the resultant reaction liquid and extraction was performed using chloroform to obtain an organic layer. The organic layer was concentrated under reduced pressure to obtain a residue that was then dissolved in chloroform and fractionated by silica gel column chromatography (hexane:ethyl acetate=10:1). Methanol was added to a fraction containing the target product and cooling thereof was performed to precipitate a solid. The solid was filtered off, was washed with cold methanol, and was subsequently dried under reduced pressure to yield 20.8 g (74% yield) of N,N'-dibenzyl-N,N'-bis[4-(pentan-3 -yl amino)phenyl]ethane-1,2-diamine (compound I-4) represented by the following formula.

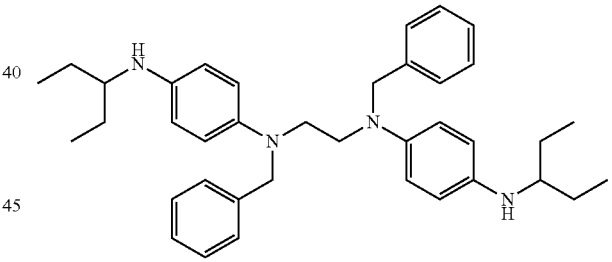

(I-4)

Properties: White solid
Melting point: 81° C.
$^1$H-NMR (300 MHz, CDCl$_3$, δ ppm): 0.91 (t, 12H), 1.49 (m, 8H), 3.07 (m, 4H), 3.41 (s, 4H), 4.35 (s, 4H), 6.47 (d, 4H), 6.56 (d, 4H), 7.23 (m, 12H)

Production Example 5

Production of N,N'-bis[4-(diisopropyl amino)phenyl]-N,N'-diisopropylethane-1,2-diamine (compound I-5)

First, 282.8 g of acetone and 14.1 g of sodium cyanoborohydride were added to a solution of 20.0 g of N,N'-diisopropyl-N,N'-bis[4-(isopropylamino)phenyl]ethane-1,2-diamine (compound I-2), produced by the method in Production Example 2, in 300 mL of methanol at room temperature. Thereafter, the solution was stirred for 3 days at 60° C. while adjusting the solution to a pH of 6.9-7.4 using acetic acid. The resultant reaction liquid was concentrated under reduced pressure to obtain a residue. After 5N sodium hydroxide aqueous solution had been added to the residue, stirring was performed for 1 hour at room temperature. Extraction of the reaction liquid was performed using ethyl acetate to obtain an organic layer that was then washed with water and concentrated under reduced pressure. The resultant residue was purified by silica gel column chromatography (hexane:ethyl acetate=1:1) to yield 17.01 g (70.6% yield) of N,N'-bis[4-(diisopropyl amino)phenyl]-N,N'-diisopropylethane-1,2-diamine (compound I-5) represented by the following formula.

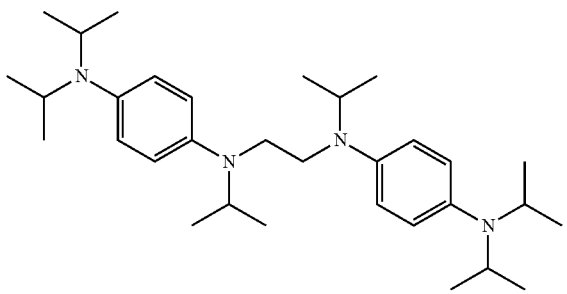

(I-5)

Properties: Brown solid

Melting point: 71° C.

$^1$H-NMR (500 MHz, DMSO-D$_6$, δ ppm): 0.98 (d, 24H), 1.07 (d, 12H), 3.10 (m, 4H), 3.50 (m, 4H), 3.80 (m, 2H), 6.70 (d, 4H), 6.85 (d, 4H)

Production Example 6

Production of N,N'-bis(4-anilinophenyl)-N,N'-diisopropyldecane-1,10-diamine (compound I-6)

(1) Production of N,N'-bis(4-anilinophenyl)-N,N'-bis(isopropyl)sebacamide

After 5.6 g of triethylamine had been added to a solution of 10.0 g of N-isopropyl-N'-phenyl-p-phenylenediamine in 110 mL of toluene, the solution was ice cooled and 4.4 g of sebacoyl chloride was further added thereto by dripping. Stirring was performed for 16 hours at 40° C. and, after 200 mL of water had been added to the resultant reaction liquid, the reaction liquid was filtered to obtain a solid. The solid was crushed and washed with isopropyl alcohol and was dried under reduced pressure to yield 10.5 g (92% yield) of N,N'-bis(4-anilinophenyl)-N,N'-bis(isopropyl)sebacamide as an gray-white solid.

(2) Production of N,N'-bis(4-anilinophenyl)-N,N'-diisopropyldecane-1,10-diamine (compound I-6)

A suspension of 1.4 g of lithium aluminum hydride in 70 mL of dehydrated tetrahydrofuran was prepared and 3.0 g of N,N'-bis(4-anilinophenyl)-N,N'-bis(isopropyl)sebacamide was added thereto under ice cooling. The suspension was returned to room temperature and stirred for 1 hour, and was subsequently heated under reflux overnight. The resultant reaction liquid was ice cooled and, after 30 mL of water and 5 mL of 1N sodium hydroxide aqueous solution had been added thereto, was stirred and then filtered using Celite. Chloroform was added to the filtrate and liquid separation was performed to obtain an organic layer. The organic layer was dried using anhydrous magnesium sulfate and was subsequently concentrated under reduced pressure. The resultant solid was washed with ethyl acetate and dried under reduced pressure to yield 2.8 g (97% yield) of N,N'-bis(4-anilinophenyl)-N,N'-diisopropyldecane-1,10-diamine (compound I-6) represented by the following formula.

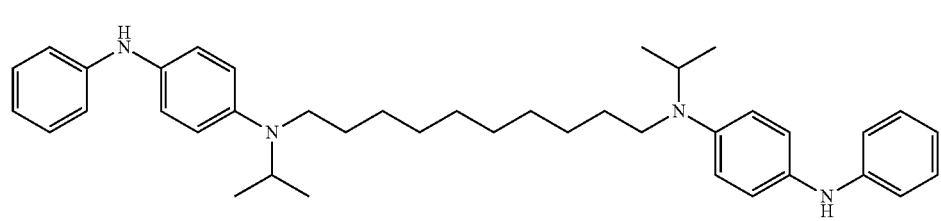

(I-6)

Properties: White solid

Melting point: 80° C.

$^1$H-NMR (300 MHz, DMSO-D$_6$, δ ppm): 1.06 (d, 12H), 1.26 (m, 12H), 1.42 (m, 4H), 3.00 (t, 4H), 3.83 (m, 2H), 6.62 (dd, 2H), 6.68 (d, 4H), 6.83 (d, 4H), 6.94 (d, 4H), 7.10 (dd, 2H), 7.59 (s, 2H)

Production Example 7

Production of N,N'-bis(4-anilinophenyl)-N,N'-bis(4-methylpentan-2-yl)oxamide (compound I-7)

After 1.31 g of pyridine had been added to a solution of 4.44 g of N-1,3-dimethylbutyl-N'-phenyl-p-phenyl enedi amine in 40 mL of tetrahydrofuran, the solution was ice cooled and a solution of 1.0 g of oxalyl chloride in 5 mL of tetrahydrofuran was further added thereto by dripping.

The solution was stirred for 2 days at room temperature and was then ice cooled again. Water and ethyl acetate were added and liquid separation was performed to obtain an organic layer. The organic layer was washed with 1N hydrochloric acid, saturated sodium hydrogen carbonate aqueous solution, and saturated saline in this order, was dried using anhydrous magnesium sulfate, and was concentrated under reduced pressure. Precipitated solid was washed with a mixed liquid of diisopropyl ether and hexane to yield 3.99 g (86% yield) of N,N'-bis(4-anilinophenyl)-N,N'-bis(4-methylpentan-2-yl)oxamide (compound I-7) represented by the following formula.

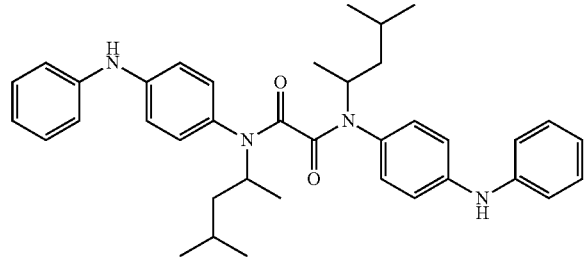

(I-7)

Properties: Blue-purple solid

Melting point: 187-188° C.

$^1$H-NMR (300 MHz, DMSO-D$_6$, δ ppm): 0.85 (m, 24H), 4.48 (m, 2H), 6.88 (m, 6H), 7.11 (m, 8H), 7.27 (m, 4H), 8.39 (m, 2H)

Production Example 8

Production of N,N'-bis(4-anilinophenyl)-N,N'-bis(4-methylpentan-2-yl)adipamide (compound I-8)

A suspension of 20 g of adipic acid in 40 mL of chloroform was prepared and, after 65.2 g of thionyl chloride and one drop of N,N-dimethylformamide had been added thereto, the suspension was heated under reflux for 8 hours. Chloroform and excess thionyl chloride were distilled from the resultant reaction liquid by heating under normal pressure to obtain a residue that was subsequently dissolved in 30 mL of dehydrated tetrahydrofuran. The resultant solution was dripped into an ice-cooled solution of 73.5 g of N-1,3-dimethylbutyl-N'-phenyl-p-phenylenediamine and 26.0 g of pyridine in 500 mL of dehydrated tetrahydrofuran and was returned to room temperature before being stirred overnight. After water and diisopropyl ether had been added to the resultant reaction liquid, the reaction liquid was filtered to obtain a solid. The solid was crushed and washed with water, methanol, and diisopropyl ether in this order, and was dried under reduced pressure to yield 34.5 g (39% yield) of N,N'-bis(4-anilinophenyl)-N,N'-bis(4-methylpentan-2-yl) adipamide (compound I-8) represented by the following formula.

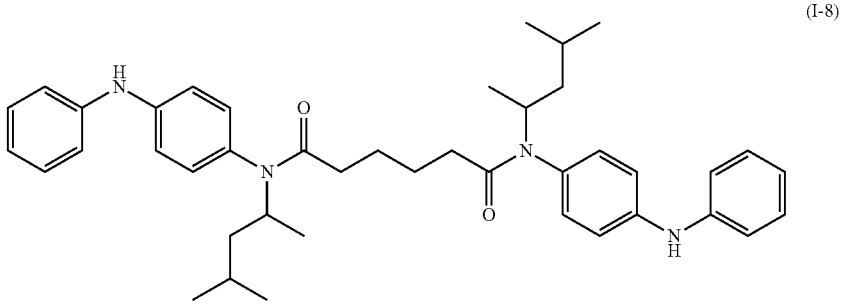 [SMILES: CC(C)CC(C)N(C(=O)CCCCC(=O)N(c1ccc(Nc2ccccc2)cc1)C(C)CC(C)C)c1ccc(Nc2ccccc2)cc1]

(I-8)

Properties: Pale purple solid

Melting point: 204-206° C.

$^1$H-NMR (300 MHz, DMSO-D$_6$, δ ppm): 0.96 (m, 20H), 1.20 (m, 6H), 1.55 (m, 2H), 1.75 (br-s, 4H), 4.82 (m, 2H), 6.86 (m, 6H), 7.08 (m, 8H), 7.24 (m, 4H), 8.31 (s, 2H)

Compounds I-9 to I-14 shown below in Table 1 were each produced in accordance with a method in one of the above production examples. The Physico-chemical properties of these compounds are shown in Table 2.

TABLE 1

| Compound number | Compound |
|---|---|
| I-9 | |

TABLE 1-continued

| Compound number | Compound |
|---|---|
| I-10 | 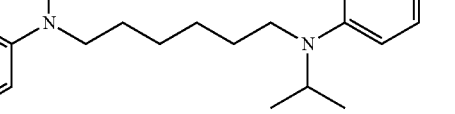 |
| I-11 | 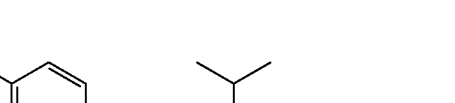 |
| I-12 | 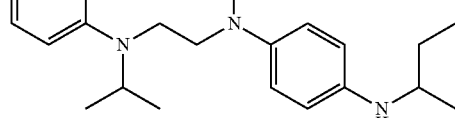 |
| I-13 |  |
| I-14 | 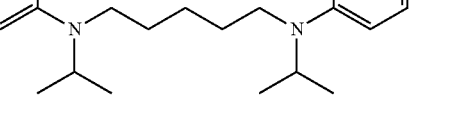 |

TABLE 2

| Number | Properties | $^1$H-NMR data |
|---|---|---|
| I-9 | Yellow solid<br>Melting point 84° C. | $^1$H-NMR (300 MHz, CDCl$_3$, δ ppm): 1.06 (t, 6H), 1.18 (d, 12H), 3.20 (q, 4H), 3.27 (s, 4H), 3.54 (dq, 2H), 4.75 (br-s, 2H), 6.58 (d, 4H), 6.67 (d, 4H) |
| I-10 | Black oil | $^1$H-NMR (300 MHz, CDCl$_3$, δ ppm): 1.06 (d, 12H), 1.16 (d, 12H), 1.27 (br-s, 4H), 1.42 (br-s, 4H), 2.96 (m, 4H), 3.53 (dq, 2H), 3.64 (dq, 2H), 6.54 (d, 4H), 6.73 (d, 4H) |
| I-11 | Dark ocher oil | $^1$H-NMR (300 MHz, DMSO-D$_6$, δ ppm): 0.86 (t, 12H), 0.95 (d, 12H), 1.35 (m, 16H), 2.89 (br-s, 4H), 3.17 (m, 2H), 3.50 (m, 2H), 4.67 (d, 2H), 6.46 (m, 4H), 6.64 (m, 4H) |
| I-12 | Pale ocher solid<br>Melting point 89-90° C. | $^1$H-NMR (300 MHz, DMSO-D$_6$, δ ppm): 1.09 (d, 12H), 1.35 (m, 2H), 1.47 (m, 4H), 3.02 (m, 4H), 3.85 (m, 2H), 6.63 (m, 2H), 6.73 (m, 4H), 6.85 (m, 4H), 6.94 (m, 4H), 7.11 (m, 4H), 7.62 (s, 2H) |

TABLE 2-continued

| Number | Properties | $^1$H-NMR data |
|---|---|---|
| I-13 | Black oil | $^1$H-NMR (300 MHz, DMSO-D$_6$, δ ppm): 0.85 (m, 12H), 1.01 (d, 6H), 1.18 (m, 4H), 1.41 (m, 4H), 1.56 (m, 2H), 2.98 (m, 4H), 3.73 (m, 2H), 6.61 (dd, 2H), 6.70 (d, 4H), 6.82 (d, 4H), 6.93 (d, 4H), 7.08 (dd, 2H), 7.59 (s, 2H) |
| I-14 | Blue-purple solid Melting point 187-188° C. | $^1$H-NMR (300 MHz, DMSO-D$_6$, δ ppm): 1.07 (d, 12H), 1.33 (m, 4H), 1.44 (m, 4H), 3.01 (m, 4H), 3.85 (m, 2H), 6.62 (dd, 2H), 6.70 (d, 4H), 6.83 (d, 4H), 6.95 (d, 4H), 7.10 (dd, 2H), 7.59 (s, 2H) |

Rubber compositions were produced by a standard method according to formulations 1 and 2 shown in Table 3. However, note that the blending amounts of various bisphenyldiamine compounds and anti-aging agents were changed depending on the example (refer to Tables 4 and 5 described further below). Formulation 1 is a formulation for a rubber composition that it is envisaged will be used in a tire tread and formulation 2 is a formulation for a rubber composition that it is envisaged will be used in a tire sidewall. Each of the produced rubber compositions was vulcanized by a standard method. Ozone resistance and discoloration of the resultant vulcanized rubber compositions were evaluated by the methods described further below.

TABLE 3

| | Formulations | |
|---|---|---|
| | Formulation 1 | Formulation 2 |
| Type of component | Parts by mass | Parts by mass |
| SBR *1 | 100 | — |
| BR | — | 50 |
| Natural rubber | — | 50 |
| Carbon black A *2 | 25 | — |
| Carbon black B *3 | — | 50 |
| Silica *4 | 25 | — |
| Silane coupling agent *5 | 2 | — |
| Stearic acid | 2 | 2 |
| Wax *6 | 2 | 2 |
| Zinc oxide | 3 | 3 |
| Vulcanization accelerator DPG *7 | 1.0 | 0.3 |
| Vulcanization accelerator MBTS *8 | 1.0 | 0.3 |
| Vulcanization accelerator CBS *9 | 1.0 | 0.8 |
| Sulfur | 1.5 | 2.0 |
| Bisphenyldiamine compound X *10 | Variable amount (refer to Tables 4 and 5) | |
| Bisphenyldiamine compound Y *11 | Variable amount (refer to Tables 4 and 5) | |
| Bisphenyldiamine compound Z *12 | Variable amount (refer to Tables 4 and 5) | |
| Anti-aging agent 6PPD *13 | Variable amount (refer to Tables 4 and 5) | |
| Anti-aging agent TMQ *14 | Variable amount (refer to Tables 4 and 5) | |

*1 SBR: Styrene-butadiene copolymer rubber, #1500 produced by JSR Corporation
*2 Carbon black A: SEAST 7HM produced by Tokai Carbon Co., Ltd.
*3 Carbon black B: SEAST F produced by Tokai Carbon Co., Ltd.
*4 Silica: Nipsil VN3 produced by Tosoh Silica Corporation
*5 Silane coupling agent: Bis(3-ethoxysilylpropyl)tetrasulfide
*6 Wax: Microcrystalline wax, Ozoace 0701 produced by Nippon Seiro Co., Ltd.
*7 Vulcanization accelerator DPG: NOCCELER D produced by Ouchi Shinko Chemical Industrial Co., Ltd.
*8 Vulcanization accelerator MBTS: NOCCELER DM produced by Ouchi Shinko Chemical Industrial Co., Ltd.

TABLE 3-continued

| | Formulations | |
|---|---|---|
| | Formulation 1 | Formulation 2 |

*9 Vulcanization accelerator CBS: SANCELER CM-G produced by Sanshin Chemical Industry Co., Ltd.
*10 Bisphenyldiamine compound X: Compound I-2 produced in Production Example 2
*11 Bisphenyldiamine compound Y: Compound I-4 produced in Production Example 4
*12 Bisphenyldiamine compound Z: Compound I-7 produced in Production Example 7
*13 Anti-aging agent 6PPD: NOCRAC 6C produced by Ouchi Shinko Chemical Industrial Co., Ltd., N-phenyl-N'-(1,3-dimethylbutyl)-p-phenylenediamine
*14 Anti-aging agent TMQ: NONFLEX RD-S produced by Seiko-Chemical Co., Ltd., polymerized 2,2,4-trimethyl-1,2-dihydroquinoline <Ozone Resistance>

A test piece of each of the rubber compositions was subjected to an ozone degradation test in accordance with JIS K6301 under conditions of a temperature of 40° C., an ozone concentration of 50 pphm, and elongation of 20%. After 50 hours had passed, the state of degradation of the test piece was inspected and was evaluated using the following three-level scale based on the number of cracks that had formed.

A: Small number of cracks

B: Large number of cracks

C: Countless number of cracks

Moreover, the test piece was evaluated using the following five-level scale based on the size and depth of cracks.

1: Cracks not visible by naked eye but visible under ×10 magnifying glass

2: Cracks visible by naked eye

3: Deep and relatively large cracks (less than 1 mm)

4: Deep and large cracks (at least 1 mm and less than 3 mm)

5: Cracks of at least 3 mm or severing likely to occur

Note that in a situation in which cracks were not observed, an evaluation of "no cracks" was given. The results of this evaluation are shown in Tables 4 and 5.

<Discoloration>

After each of the test pieces had been subjected to the ozone degradation test described above, surface discoloration of the test piece was visually evaluated using the following four-level scale. The results of this evaluation are shown in Tables 4 and 5.

A$^+$: Black and glossy

A: Black but not glossy

A$^-$: Surface discoloration confirmed

F: Discoloration of entire surface

TABLE 4

|  | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Formulation | 1 | 2 | 2 | 2 | 2 | 2 | 2 | 2 | 2 | 2 | 2 |
| Bisphenyldiamine compound X | 1 | 0.2 | 1 | 3 | 6 | 10 | 3 | 1.5 | 1.5 | — | — |
| Bisphenyldiamine compound Y | — | — | — | — | — | — | — | — | — | 3 | — |
| Bisphenyldiamine compound Z | — | — | — | — | — | — | — | — | — | — | 3 |
| Anti-aging agent 6PPD | — | — | — | — | — | — | — | 1.5 | 1.5 | — | — |
| Anti-aging agent TMQ | 0.3 | — | — | — | — | — | 1 | — | 1 | — | — |
| Ozone resistance | A-2 | A-3 | A-2 | No cracks | No cracks | No cracks | No cracks | No cracks | No cracks | A-2 | A-2 |
| Discoloration | A+ | A+ | A+ | A | A− | A− | A+ | A | A | A | A |

TABLE 5

|  | Comparative Example 1 | Comparative Example 2 | Comparative Example 3 | Comparative Example 4 | Comparative Example 5 | Comparative Example 6 |
|---|---|---|---|---|---|---|
| Formulation | 1 | 2 | 2 | 2 | 2 | 2 |
| Bisphenyldiamine compound X | — | — | — | — | — | — |
| Bisphenyldiamine compound Y | — | — | — | — | — | — |
| Bisphenyldiamine compound Z | — | — | — | — | — | — |
| Anti-aging agent 6PPD | 1 | 1 | 3 | 6 | 10 | 3 |
| Anti-aging agent TMQ | 0.3 | — | — | — | — | 1 |
| Ozone resistance | B-3 | B-4 | A-3 | A-2 | A-1 | A-2 |
| Discoloration | A | A | A− | F | F | A− |

From Tables 4 and 5, it can be seen that in the case of rubber compositions that contained the bisphenyldiamine compound represented by formula (I) blended with at least one rubber component selected from natural rubber and diene-based synthetic rubbers, and also in the case of rubber compositions according to the present disclosure that contained another anti-aging agent in combination with the bisphenyldiamine compound represented by formula (I), weather resistance was improved and surface discoloration was inhibited compared to rubber compositions that only contained conventional anti-aging agents.

The invention claimed is:

1. A bisphenyldiamine compound represented by formula (I) shown below

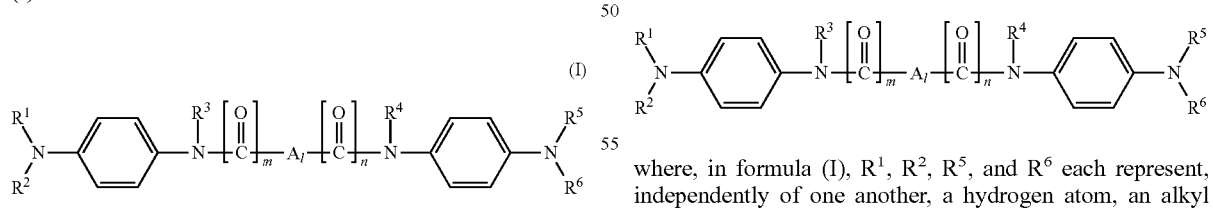

(I)

where, in formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1, wherein either (i) at least one of $R^1$, $R^2$, $R^5$, or $R^6$ is a phenyl group, at least of one l, m, or n is 1, and m=n, or (ii) one of $R^1$ and $R^2$ is a hyfrogen atom, one of $R^5$ and $R^6$ is a hydrogen atom, and m=n=1.

2. An anti-aging agent for natural rubber and diene-based synthetic rubber-use comprising the bisphenyldiamine compound of claim 1.

3. A rubber composition comprising
at least one rubber component selected from natural rubber and diene-based synthetic rubbers and, blended therewith, at least one bisphenyldiamine compound represented by formula (I) shown below (I)

where, in formula (I), $R^1$, $R^2$, $R^5$, and $R^6$ each represent, independently of one another, a hydrogen atom, an alkyl group having a carbon number of 1-10, or a phenyl group, but $R^1$ and $R^2$ do not both simultaneously represent a hydrogen atom and $R^5$ and $R^6$ do not both simultaneously represent a hydrogen atom, $R^3$ and $R^4$ each represent, independently of one another, an alkyl group having a carbon number of 1-8 or an aralkyl group, A represents an alkylene group having a carbon number of 1-12, and l, m, and n each represent an integer of 0 or 1, wherein either (i) at least one of $R^1$, $R^2$, $R^5$, or $R^6$ is a phenyl group, at least one of l, m or n is 1, and m=n, or (ii) m=n=1.

4. The rubber composition of claim 3, wherein
in the at least one bisphenyldiamine compound represented by formula (I), $R^3$ and $R^4$ are each an alkyl group having a carbon number of 1-8, A is an alkylene group having a carbon number of 1-8, l is 1, and m and n are each 0.

5. The rubber composition of claim 3, wherein
a blending amount of the at least one bisphenyldiamine compound represented by formula (I) is in a range of from 0.2 parts by mass to 10 parts by mass relative to 100 parts by mass of the at least one rubber component.

6. A tire comprising a tire member comprising the rubber composition of claim 3.

7. The tire of claim 6, wherein
the tire member is either or both of a tread and a sidewall.

* * * * *

UNITED STATES PATENT AND TRADEMARK OFFICE
CERTIFICATE OF CORRECTION

PATENT NO. : 10,011,704 B2
APPLICATION NO. : 15/312768
DATED : July 3, 2018
INVENTOR(S) : Aya Saiki et al.

Page 1 of 1

It is certified that error appears in the above-identified patent and that said Letters Patent is hereby corrected as shown below:

In the Claims

Claim 1, Column 28, Line 37, please delete "at least of one 1," and insert --at least one of 1,--, Claim 1, Column 28, Line 38, please delete "hyfrogen" and insert --hydrogen--.

Signed and Sealed this
Fourth Day of September, 2018

Andrei Iancu
*Director of the United States Patent and Trademark Office*